United States Patent [19]
Mason et al.

[11] Patent Number: 5,232,020
[45] Date of Patent: Aug. 3, 1993

[54] SHUTOFF VALVE HAVING A UNITARY VALVE BODY

[75] Inventors: Jeffrey T. Mason, Escondido; Bradley R. Mason, Olivenhain, both of Calif.

[73] Assignee: Breg, Inc., Vista, Calif.

[21] Appl. No.: 906,409

[22] Filed: Jul. 1, 1992

Related U.S. Application Data

[63] Continuation-in-part of Ser. No. 767,494, Sep. 30, 1991, which is a continuation-in-part of Ser. No. 578,508, Sep. 5, 1990, Pat. No. 5,080,089.

[51] Int. Cl.⁵ .............................................. F16L 29/00
[52] U.S. Cl. ............................... 137/614.04; 137/315; 137/454.2
[58] Field of Search ............... 137/614, 614.04, 15, 137/315, 454.2

[56] References Cited

U.S. PATENT DOCUMENTS 2,819,914 1/1958 Eitner ..................... 137/614.04 X
3,520,331 7/1970 Locke et al. ................. 137/614.04
4,509,554 4/1985 Failla ........................ 137/329.1 X Primary Examiner—John C. Fox
Attorney, Agent, or Firm—Rodney F. Brown

[57] ABSTRACT

A shutoff valve is provided having a body enclosing a chamber that defines a continuous fluid passageway. A plunger resides in the chamber and is slidably positionable between a closed position wherein the fluid passageway is occluded and an open position wherein the fluid passageway enables fluid flow therethrough. A sealing member is also positioned in the passageway, which circumscribes the plunger to effectuate a seal when the plunger is in the closed position. A spring is compressibly mounted in the fluid passageway against the plunger to bias the plunger in the closed position. The chamber is characterized by a series of fluid-communicating sections formed therein which cooperate with a plurality of stages integrally positioned on the plunger to define the manner in which the valve is assembled and operated.

20 Claims, 3 Drawing Sheets

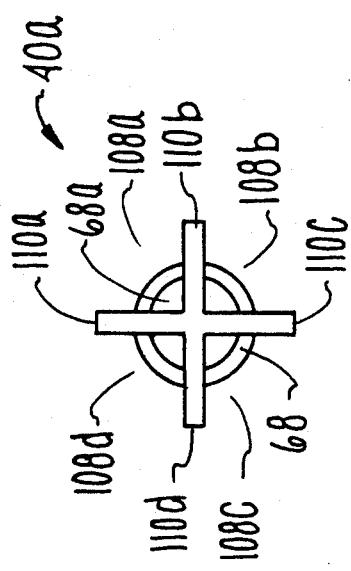
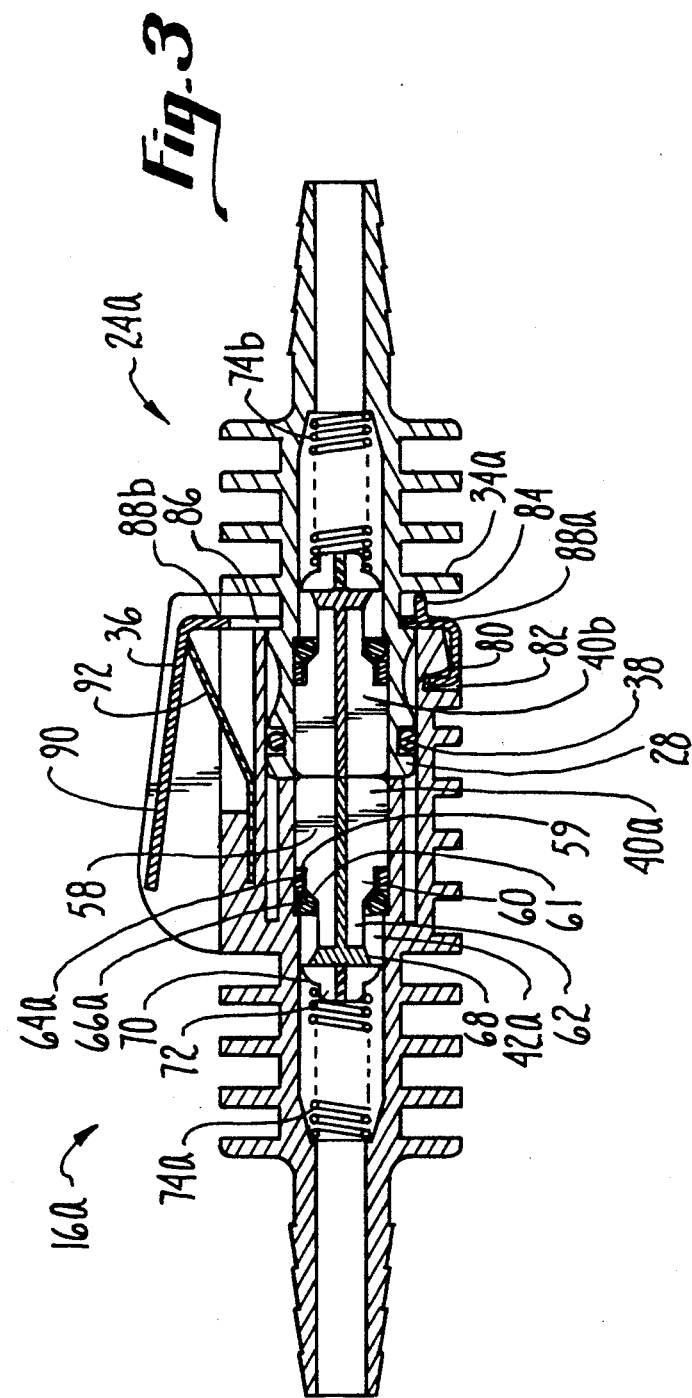

SHUTOFF VALVE HAVING A UNITARY VALVE BODY

This application is a continuation-in-part patent application of our prior co-pending patent application entitled, "Therapeutic Nonambient Temperature Fluid Circulation System", Ser. No. 767,494 filed on Sept. 30, 1991, which is a continuation-in-part application of our patent application entitled, "Therapeutic Apparatus Applying Compression and a Nonambient Temperature Fluid," Ser. No. 578,508 filed on Sept. 5, 1990, U.S. Pat. No. 5,080,089.

TECHNICAL FIELD

The present invention relates generally to a shutoff valve and more particularly to a shutoff valve having a unitary body and a spring-biased plunger nested therein.

BACKGROUND OF THE INVENTION

Many valve coupling configurations are well known in the art as evidenced, for example, by U.S. Pat. Nos. 4,436,125; 4,541,457; and 4,934,655. Although such valves may be operationally effective, they are relatively expensive to manufacture and assemble due to their complex structure. In particular, assembly of prior art valves preliminarily requires manufacture of the valve body in a plurality of pieces to enable placement of the plunger in the body during valve assembly. After the plunger is placed in the body, assembly of the valve is completed by gluing or welding the pieces of the body together. This step is particularly cost intensive.

As such a need exists for a valve having utility in a valve coupling which is effective in its operation, yet simple and inexpensive to manufacture and assemble. In particular, a valve is needed which can be assembled from a one-piece molded body to avoid gluing or welding of parts during assembly. Such a valve is further needed which can provide reliable performance during repeated use without maintenance.

SUMMARY OF THE INVENTION

The present invention is a shutoff valve comprising a one-piece molded valve body. Formed in the valve body is a valve chamber that defines a continuous fluid passageway through the body. A valve plunger is nested within the chamber and is slidably positionable between a closed position, wherein the fluid passageway is occluded, and an open position, wherein the fluid passageway enables fluid flow therethrough. A sealing member and a retention member are also nested within the chamber and circumscribe the plunger to effectuate a seal when the plunger is in the closed position. The members are, however, essentially inactive when the plunger is in the open position. A spring compressibly mounted in the chamber against the plunger biases the plunger to the closed position.

The valve chamber has an exterior opening at its front end and an exterior opening at its opposite rear end. The interior of the valve chamber is partitioned into a plurality of fluid communicating sections. Specifically, a front section, a middle section and a rear section are sequentially aligned between the front and rear openings of the chamber, respectively. Adjacent sections of the chamber are distinguishable from one another by differences in their inside diameters, thus creating a shoulder between each pair of adjacent sections.

The exterior surface of the plunger is configured in stages of varying outside diameters. The outside diameter of each stage is, however, uniformly smaller than the inside diameter of corresponding sections of the chamber into which the stages are nested, thereby enabling the plunger a degree of slidable movement within the chamber.

Front and rear stages of the plunger have external surfaces which are characterized by a plurality of radially-extending axial vanes. The vanes define axial flow channels enabling fluid flow through the front and rear stages of the plunger, even when the vanes are flush with the chamber walls. An intermediate stage having the configuration of a solid frustum is provided between front and rear stages of the plunger, however, through which fluid cannot flow. Thus, fluid flow through the fluid passageway of the chamber is only possible past the intermediate frustum stage via an annular space that is provided between the frustum stage and chamber walls when the plunger is in the open position.

Assembly and operation of the present valve assembly is described hereafter in the context of the specific plunger and chamber configuration set forth above. The valve is assembled from a relatively small number of integral pieces including the body, plunger, spring, sealing member and retention member. The body is preferably a one-piece construct having the chamber formed therethrough. Such a body can be formed in a seamless unitary manner by a conventional molding method.

Assembly of the valve is initiated by inserting the spring into the rear section of the valve body. The retention and sealing members, both being ring-shaped, are then slid over the rear stages of the plunger in this prescribed order, such that they are positioned side-by-side around a narrowed front stage of the plunger immediately adjacent the frustum stage. Both members are formed from an at least somewhat resilient material, with the sealing member being substantially more resilient than the retention member.

Assembly is completed by aligning the front opening of the chamber with the rear stages of the plunger and inserting the plunger therein. The plunger is then forcibly slid deeper into the chamber. The retention and sealing members resiliently deform upon initial contact with the chamber wall enabling them to pass through the front section of the chamber and into the middle section that is of slightly greater inside diameter than the front section.

When the retention member enters the middle section, it resiliently expands to engage the wall defining the inside diameter of the middle section. As such the retention member becomes fixably seated against the sealing shoulder between the front and middle sections with the sealing member positioned behind it. Accordingly, the retention member functions to permanently retain the sealing member in the middle section. Further, with the plunger so housed in the chamber, the spring engages the rear stages of the plunger in the rear section of the chamber.

In operation, when the valve is at rest, the plunger is biased into the closed position by the expansion force of the spring. The spring presses the frustum stage forward in the chamber causing it to enter the middle section thereof and wedge firmly against the sealing member. Accordingly, the sealing member occludes the annular space between the frustum stage and the inside wall of the middle section, effectuating a complete seal thereof and preventing fluid flow through the chamber. The valve is activated by sliding the plunger rearward in the chamber against the compression force of the spring until the frustum stage separates from the sealing member and returns to the rear section of the chamber. This rearward movement of the plunger reopens the annular space between the frustum stage and the sealing member enabling the free flow of fluid through the chamber. The plunger remains in the open position only so long as a force exceeding the expansion force of the spring is maintained against it. As soon as this force is withdrawn, the plunger is returned to its closed position by the spring.

The shutoff valve of the present invention may be further provided with integral fittings extending from or formed in the body at opposite openings of the chamber. The fittings enable connection of the valve to one another or to external fixtures. For example, a plurality of the present valves may be combined in a valve coupling as disclosed in parent application Ser. No. 767,494, which is incorporated herein by reference.

In such a valve coupling, a first valve is provided with a barbed tube fitting extending from the rear opening of the chamber and a male or female connector is provided at the front opening of the chamber. A like second valve is positioned with its connector opposite the connector of the first valve. The connector of the second valve, however, has an opposite gender than that of the first valve so that they may be joined together. When so connected, the connector of each valve operates to engage the plunger of the opposing valve and slidably force the plunger into its open position. An interactive locking mechanism may additionally be provided on the housings of the two valves to fixedly maintain them coupled.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 3 is a cross-sectional elevational view of the valve coupling assembly as shown in FIG. 2, wherein the valve coupling is engaged.

FIG. 4 is a front end elevational view of the plunger of a valve as shown in FIG. 3.

DESCRIPTION OF PREFERRED EMBODIMENTS

Figure 1:
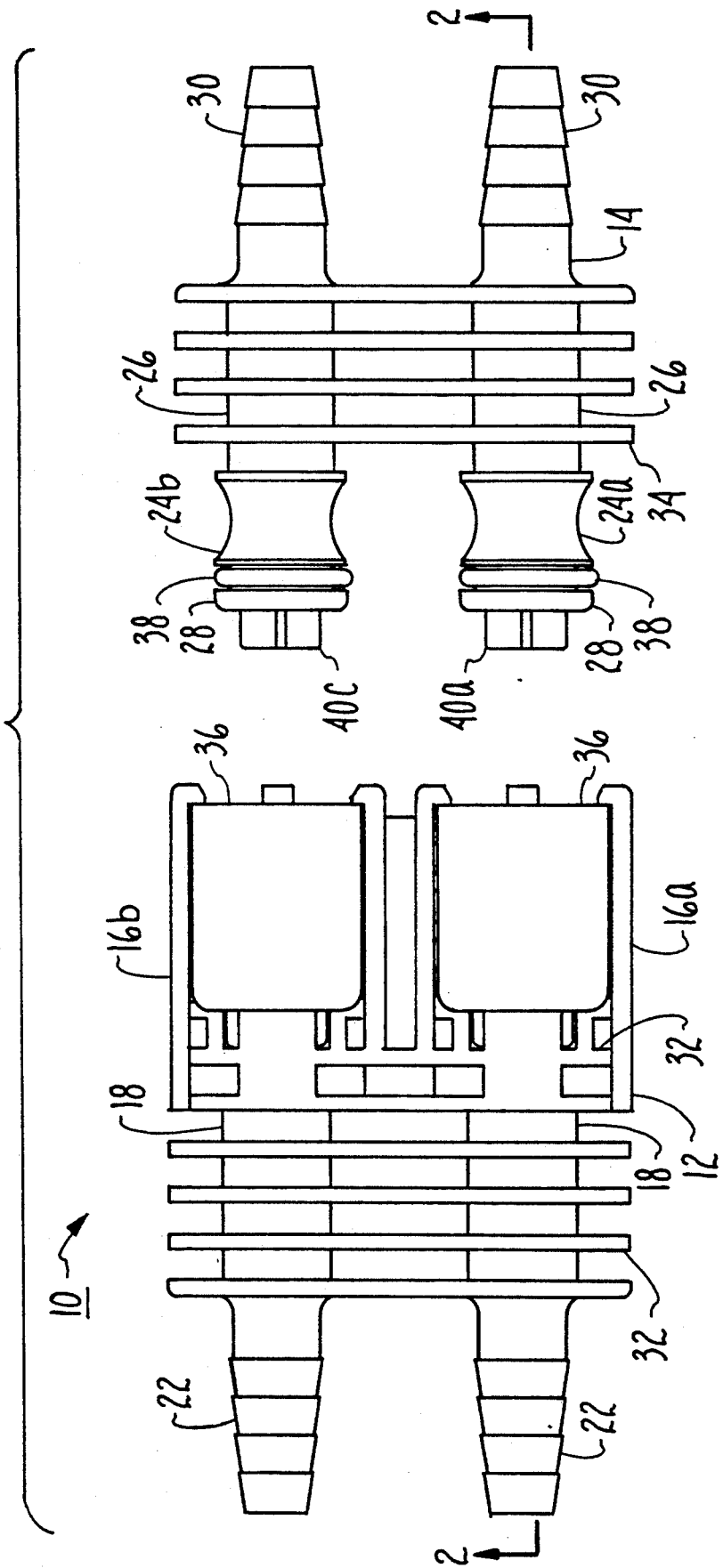
FIG. 1 is a perspective view of a plurality of valves of the present invention as they are employed in a valve coupling, wherein the valve coupling is disengaged.

Referring initially to FIG. 1, a valve coupling is shown and generally designated as 10. Valve coupling 10 is made up of a female coupling unit 12 and a male coupling unit 14 which are interconnectable. Female coupling unit 12 comprises two identical parallely-aligned valves 16a, 16b. Each valve 16a, 16b has a body 18 with a female connector 20 and a tube fitting 22 at opposite ends of body 18. Male coupling unit 14 likewise comprises two identical parallely-aligned valves 24a, 24b, each having a body 26 with a male connector 28 and a tube fitting 30 at opposite ends of body 26.

A plurality of rib members 32 maintain valves 16a, 16b integral with female coupling unit 12 and in fixed alignment relative to each other. Similarly, a plurality of rib members 34 maintain valves 24a, 24b integral with male coupling unit 14 and in fixed alignment relative to each other. Furthermore, rib members 32 and 34 fixably align valves 16a, 16b and 24a, 24b respectively such that female coupling unit 12 is capable of connection to male coupling unit 14 with male connectors 28 being received by female connectors 20 in a manner shown hereafter.

Female coupling unit 12 and male coupling unit 14 are preferably each formed as a single unitary structure. Conventional molding techniques can be used to achieve this result. A preferred material for units 12 and 14 is a high-strength rigid plastic material, such as a DELRIN plastic. By forming each unit 12, 14 as a one-piece construct, economies in assembly of the couplings are realized by eliminating any added steps of gluing or welding disparate parts together.

Additionally shown in FIG. 1 is a locking element 36 mounted on each female connector 20. Locking elements 36 are preferably formed from a resilient sheet material such as plastic or metal, e.g., stainless steel, and are individually mounted on female coupling unit 12 subsequent to fabrication of unit 12 and locking elements 36. Finally, an external o-ring 38 is mounted on each male connector 28 and is preferably formed from a resilient elastomeric material. External o-rings rings 38 are likewise preferably individually mounted on male coupling unit 14 subsequent to fabrication of unit 14 and external o-rings 38.

Figure 2:
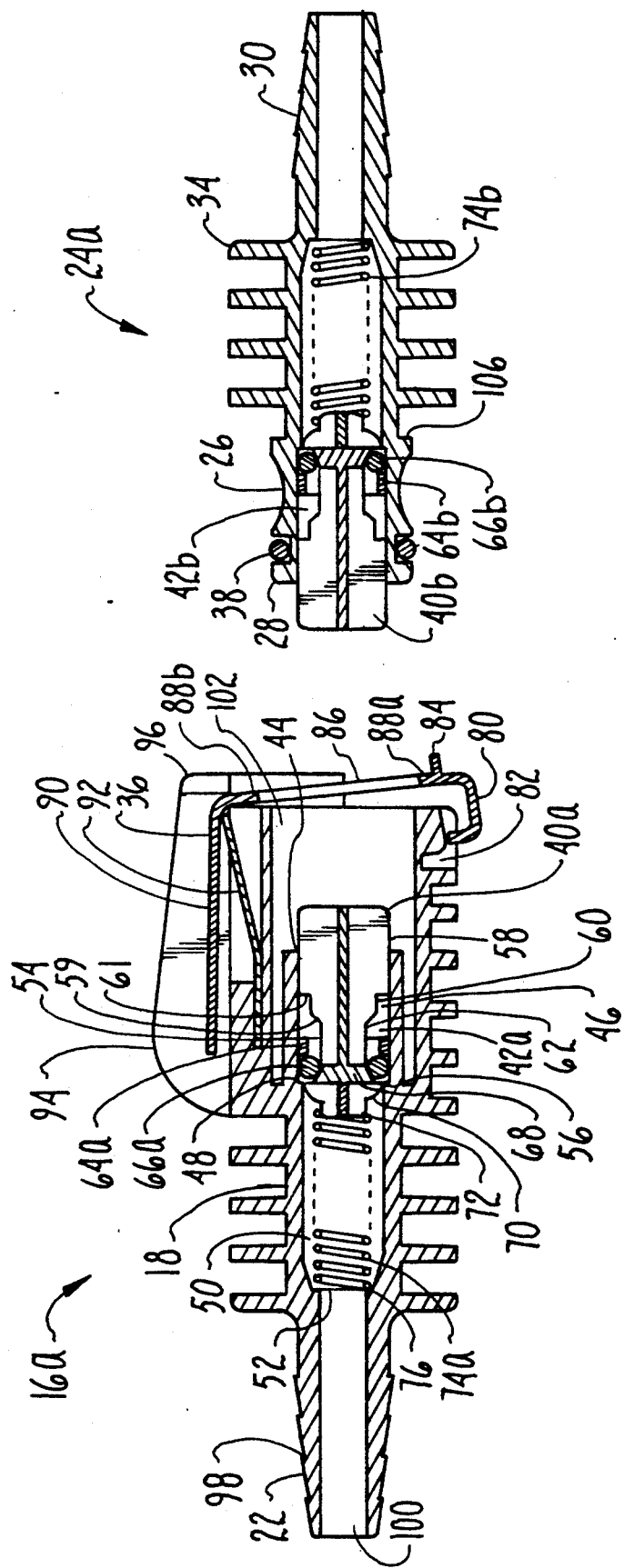
FIG. 2 is a cross-sectional elevational view of the valve coupling as shown along line 2—2 in FIG. 1, wherein the valve coupling is disengaged.

Plungers 40a and 40c are partially shown extending from valves 24a and 24b respectively. These and other internal components of the valves of the present invention, as represented in FIGS. 2 and 3 by valves 16a and 24a, are further described with initial reference to FIG. 2. Referring to valve 16a in FIG. 2, body 18 is shown to enclose a chamber 42a defining a continuous fluid passageway with a plunger 40a slidably positioned therein. Chamber 42a has in succession a front opening 44, a front section 46, a middle section 48, a rear section 50, and a rear opening 52. The inside diameter of middle section 48 is greater than that of adjacent front section 46, such that a sealing shoulder 54 is formed therebetween. Likewise, the inside diameter of middle section 48 is greater than that of adjacent rear section 50, thereby forming a restraint shoulder 56 between sections 48 and 50. It is also noted that rear section 50 downsizingly tapers toward rear opening 52.

Plunger 40a is formed with a plurality of stages, each of which has an outside diameter that is sized to be at least slightly smaller than the inside diameters of preselected sections of chamber 42a or other interior components contained within the sections. In particular, plunger 40a is made up of three front stages 58, 60, 62 having successively decreasing outside diameters. Thus, a first shoulder 59 is formed between stages 58 and 60 and a second shoulder 61 is formed between stages 60 and 62.

First stage 58 is sized to fit closely, but slidably, within front section 46, while second stage 60 is sized to fit closely, but slidably, within a retention member 64a positioned in middle section 48, retention member 64a having a lesser inside diameter than front section 46. Finally, third stage 62 is sized to fit within a sealing member 66a of lesser inside diameter than retention member 64a, sealing member 66a also being positioned in middle section 48. Adjacent to third stage 62 is an intermediate frustum-shaped stage 68 that is sized relative to sealing member 66a as described below.

Plunger 40a has two rear stages 70, 72. First rear stage 70 is sized to fit closely, but slidably, within rear section 50. Second rear stage 72 has an outside diameter less than that of first rear stage 70, thereby forming a node at the rear of plunger 40a. A coil spring 74a having a diameter greater than rear opening 52 resides in rear section 50. Rear end 76 of spring 74a abuts the tapered wall of rear section 50 which further restricts spring 74a from exiting rear opening 52. Front end 78 of spring 74a fits over the node of second rear stage 72, resting on first rear stage 70 and exerting a forward expansion force against plunger 40.

As noted above, positioned around plunger 40a is sealing member 66a that resides within middle section 48 throughout the entire operation of valve 16a. The inside diameter of sealing member 66a is smaller than the minimum outside diameter of frustum stage 68, but larger than the maximum outside diameter of frustum stage 68. Sealing member 66a is a gasket preferably in the form of an internal o-ring fabricated from a resilient elastomeric material capable of substantial elastic deformation, such as natural or synthetic rubber.

Retention member 64a is ring-shaped to enable positioning around plunger 40a and stationarily resides within middle section 48 throughout the entire operation of valve 16a. the inside diameter of retention member 64a is greater than the outside diameter of sealing member 66a such that sealing member 66a cannot pass through retention member 64a. Additionally, the outside diameter of retention member 64a is at least about equal to the inside diameter of middle section 48 such that retention member 64a, being somewhat resilient, is fixably maintained by compression against the wall of middle section 48 and sealing shoulder 54. Retention member 64a is preferably fabricated from a hard plastic, such as the same DELRIN plastic forming bodies 18, 26, which is somewhat resilient, although substantially less resilient than sealing member 66a.

A locking mechanism is further provided for fixably coupling valve 16a with valve 24a. The locking mechanism comprises a locking element 36 having a catch 80 receivable within slot 82 of female connector 20. Extending forwardly from locking element 36 to engage valve 24a is an activating member 84. An opening 86 for receiving male connector 28 is formed through locking element 36, opening 86 having a lower edge 88a and an upper edge 88b. Positioned on locking element 36 opposite catch 80 is a release lever 90. Release lever 90 abuts a tension spring 92 integral with body 18. Further integral with body 18 is a sidewall 94 and peg 96 for retaining locking element 36.

Tubing connector 22, that is positioned at the rear of valve 16a, is provided with a plurality of successive barbs 98 of expanding diameter in a forward direction for sealably retaining an elastic tube from a fluid source (not shown) which is placed over barbs 98 to enable the transport of fluids into or out of valve 16a via port 100. A port 102 is further provided at the front of valve 16a for passing fluids into or out of valve 16a preferably via coupled valve 24a.

The internal components, i.e., fluid passageway 40b, plunger 40b, coil spring 74b, retention member 64b, and sealing member 66b, of valve 24a are substantially identical to those of valve 16a. Valve 24a is, however, externally distinguishable from valve 16a by the substitution of male connector 28 for the female connector 20 of valve 16a. Valve 24a also does not have the locking mechanism of valve 16a, but cooperates therewith by providing a stop 106 on body 26 to engage the lower edge 88a of opening 86.

It is noted that the terms "front" and "rear" are used above and hereafter to designate relative positions of valve components. By way of definition, the front of the valve refers to the end of the valve toward which the plunger is biased, while the rear refers to the opposite end of the valve.

The above-described structure of valves 16a and 24a provides for advantageous assembly thereof. In particular, it is noted that valve 16a is assembled from only a small number of parts including a unitary body 18 having a female connector 20 and tube fitting 22 integral therewith, a plunger 40a, a spring 74a, a retention member 64a, a sealing member 66a, and a locking element 36. Body 18 is a seamless one-piece construct having chamber 42a preformed therethrough. As such assembly of valve 16a requires no costly and time consuming gluing or welding of components.

Assembly is initiated by inserting spring 74a into rear section 50 via front opening 44. Retention member 64a and sealing member 66a are then placed around third front stage 62 of plunger 40a. Plunger 40a is inserted into front opening 44 and forcibly slid back in chamber 40a. Retention member 64a and sealing member 66a have outside diameters greater than the inside diameter of front section 46, but resiliently deform therein to pass through front section 46 into middle section 48 where retention member 64a expands to rest securely against the wall of middle section 48 and sealing shoulder 54. Sealing member 66a is positioned deeper within middle section 48 than retention member 64a and returns to its full expanded shape therein. Insertion of plunger 40a not only serves to seat members 64a, 66a in chamber 42a, but also enables engagement of rear stages 70, 72 with spring 74a. Once spring 74a is engaged and retention member 64a and sealing member 66a are seated, plunger 40a remains in an operational position for the life of valve 14a.

METHOD OF OPERATION

Operation of valve coupling 10 of the present invention is described below with reference to FIGS. 2–4. FIG. 2 shows valves 16a, 24a of coupling 10 in the disengaged position wherein both valves 16a, 24a are biased closed. Closure is provided in valve 16a by spring 74a urging plunger 40a forward such that first front stage 58 extends out through front opening 44. As plunger 40a moves forward, frustum stage 68 engages sealing member 66a and urges it radially outward until frustum stage 68 compresses sealing member 66a against retention member 64a and the wall of middle section 48.

Frustum stage 68 defines a continuous surface which prevents the flow of fluid therethrough, while retention member 64a and sealing member 66a cooperate to prevent the flow of fluid around frustum stage 68. Consequently, valve 16a, as shown in FIG. 2, is effectively closed to fluid flow. Valve 24a operates in essentially the same manner as described above with respect to valve 16a, thereby maintaining valve 24a closed when in a disengaged position.

FIG. 3 shows valves 16a, 24a of coupling 10 in the engaged position wherein both valves 16a, 24a are maintained open. Opening of valve 16a is provided by pressing plunger 40a of valve 16a against plunger 40b of valve 24a with sufficient force to overcome the expansion force of spring 74a thereby causing it to compress and urging plunger 40a rearward in chamber 42a. As plunger 40a withdraws into front opening 44, frustum stage 68 disengages sealing member 66a and second shoulder 61 directs sealing member 66a against restraint shoulder 56 while first shoulder 59 engages retention member 64a. Although sealing member 66a still engages plunger 40a and the inside wall of middle section 48, fluid is nevertheless able to flow through middle section 48 because of axial flow channels provided in stages 58, 60, 62, 70, and 72.

Referring to FIG. 4, flow channels 108a, 108b, 108c, 108d result from the construction of plunger 40a. The front portion of plunger 40a, i.e., stages 58, 60, 62, is shown to be constructed of orthogonal vanes 110a, 110b, 110c, 110d that provide the aforesaid flow channels. The rear portion of plunger 40a, although obstructed in this view, is of like construction. Only frustum stage 68 along with its frontal face 68a has a continuous surface which prevents the flow of fluid therethrough. However, as shown in FIG. 3, when valves 16a, 24a are in the engaged position, sealing member 66a no longer abuts frustum stage 68, thereby enabling fluid to flow around it.

Valve 16a is open to continuous fluid flow therethrough so long as spring 74a remains compressed. Plunger 40a of valve 16a further cooperates with plunger 40b of valve 24a to slidably urge plunger 40b rearward in chamber 42b enabling valve 24a to operate in essentially the same manner as described above with respect to valve 16a, thereby maintaining valve 24a open when in an engaged position.

Locking of valves 16a, 24a in the engaged position is provided by locking element 36. When female connector 20 receives male connector 28, frontal rib member 34a of valve 24a pushes activating member 84 rearward causing catch 80 to slip into slot 82. Tension spring 92 simultaneously urges the entire locking element 36 upward via release lever 90. As a result, lower edge 88a of opening 86 moves upward under stop 106 to prevent the withdrawal of valve 24a from valve 16a. Withdrawal can only be effected by depressing release lever 90 against tension spring 92 to urge catch 80 downward and out of slot 82.

While the particular valve as herein shown and disclosed in detail is fully capable of obtaining the objects and providing the advantages hereinbefore stated, it is to be understood that the valve is merely illustrative of the presently preferred embodiments of the invention and that other embodiments are possible within the scope of the present invention.

We claim:

1. A shutoff valve comprising:
   a body having a front opening with an inside diameter and a rear opening with an inside diameter;
   a chamber forming a continuous fluid passageway through said body from said front opening to said rear opening;
   a plurality of sections formed in said passageway and sequentially aligned from said front opening to said rear opening including a front section, a middle section, and a rear section, wherein said front section has a smaller inside diameter than the inside diameter of said middle section, thereby forming a sealing shoulder, and said middle section has a greater inside diameter than the inside diameter of said rear section, thereby forming a restraint shoulder;
   a multi-stage plunger slidably mounted in said chamber, said plunger slidable between an open position and a closed position, wherein said plunger has a front stage slidably engaging the inside diameter of said front section, a frustum stage slidably positionable in said middle section, and a rear stage slidably engaging the inside diameter of said rear section, further wherein said frustum stage is tapered toward said front opening and said frustum stage has a maximum diameter no greater than the inside diameter of said front opening;
   means for biasing said frustum stage toward said sealing shoulder, thereby sliding said plunger into said closed position; and
   means for sealing said fluid passageway between said frustum stage and said sealing shoulder when said plunger is in said closed position, thereby occluding said fluid passageway.

2. A shutoff valve as recited in claim 1 wherein said sealing means comprises an elastomeric o-ring positioned around said plunger and retained within said middle section of said chamber.

3. A shutoff valve as recited in claim 2 wherein said sealing means further comprises a retention ring positioned around said plunger and retained within said middle section of said chamber between said o-ring and said sealing shoulder.

4. A shutoff valve as recited in claim 3 wherein said retention ring is fixably mounted in abutment with said sealing shoulder.

5. A shutoff valve as recited in claim 3 wherein said o-ring is substantially more resilient than said retention ring.

6. A shutoff valve as recited in claim 1 wherein said biasing means is a coiled spring positioned between said middle section and said rear opening.

7. A shutoff valve as recited in claim 1 further comprising means mounted proximal to said front opening of said body for releasably engaging an opposing shutoff valve.

8. A shutoff valve as recited in claim 1 wherein said front stage extends a predetermined extension distance from said body when said plunger is in said closed position.

9. A shutoff valve as recited in claim 8 wherein said extension distance from said body is decreased when said plunger is in said open position.

10. A shutoff valve comprising:
   a body having a front opening with an inside diameter and a rear opening with an inside diameter;
   a chamber forming a continuous fluid passageway through said body from said front opening to said rear opening;
   a plurality of sections formed in said passageway and sequentially aligned from said front opening to said rear opening including a front section, a middle section, and a rear section, wherein said front section has a smaller inside diameter than the inside diameter of said middle section, thereby forming a sealing shoulder, and said middle section has a greater inside diameter than the inside diameter of said rear section, thereby forming a restraint shoulder;
   a multi-stage plunger slidably mounted in said chamber, said plunger slidable between an open position and a closed position, wherein said plunger has a front stage slidably engaging the inside diameter of said front section, a frustum stage slidably positionable in said middle section, and a rear stage slidably engaging the inside diameter of said rear section, further wherein said frustum stage is tapered toward said front opening and said frustum stage has a maximum diameter no greater than the inside diameter of said front opening;

a spring compressively positioned in said rear section, thereby biasing said frustum stage toward said sealing shoulder and sliding said plunger into said closed position; and a continuous resilient sealing member positionable between said inside diameter of said middle section and said frustum stage to occlude said fluid passageway when said plunger is in said closed position.

11. A shutoff valve as recited in claim 10 further comprising a retention member fixably positioned in abutment with said sealing shoulder.

12. A shutoff valve as recited in claim 11 wherein said front stage is segmented into three stages of diminishing outside diameter, said first stage positioned in said front section and having an outside diameter greater than the outside diameter of said second stage to form a first shoulder therebetween, said second stage slidably positionable between said front section and said middle section and having an outside diameter greater than said third stage to form a second shoulder therebetween, and said third stage slidably positionable between said middle section and said rear section.

13. A shutoff valve as recited in claim 12 wherein said second shoulder abuts said sealing member when said plunger is in said open position.

14. A shutoff valve as recited in claim 12 wherein said first shoulder abuts said retention member when said plunger is in said open position.

15. A shutoff valve as recited in claim 12 wherein said sealing member abuts said retention member when said plunger is in said closed position.

16. A shutoff valve as recited in claim 12 wherein said front stages have continuous axial flow channels formed therethrough.

17. A shutoff valve as recited in claim 10 wherein said rear stage has a diameter greater than said frustum stage.

18. A shutoff valve as recited in claim 10 wherein said rear stage has a continuous axial flow channel formed therethrough.

19. A shutoff valve coupling comprising:
a body having a front opening and a rear opening;
a female shutoff valve including a chamber forming a continuous fluid passageway through said body from said front opening to said rear opening;

a plurality of sections formed in said passageway and sequentially aligned from said front opening to said rear opening including a front section, a middle section, and a rear section, wherein said front section has a smaller inside diameter than the inside diameter of said middle section, thereby forming a sealing shoulder, and said middle section has a greater inside diameter than the inside diameter of said rear section, thereby forming a restraint shoulder;

a multi-stage plunger slidably mounted in said chamber, said plunger slidable between an open position and a closed position, wherein said plunger has a front stage slidably engaging the inside diameter of said front section, a frustum stage slidably positionable in said middle section, and a rear stage slidably engaging the inside diameter of said rear section, further wherein said frustum stage is tapered towrad said front opening and said frustum stage has a maximum diameter no greater than the inside diameter of said front opening;

means for biasing said frustum stage toward said sealing shoulder, thereby sliding said plunger into said closed position; and means for sealing said fluid passageway between said frustum stage and said sealing shoulder when siad plunger is in said closed position, thereby occuluding said fluid passageway; and a male shutoff valve comprising a body having a front opening, a rear opening and a chamber forming a continuous fluid passageway from said front opening to said rear opening, wherein said front section of said female shutoff valve is sized to receive said front opening of said male shutoff valve body, thereby providing fluid communication between said female valve chamber and said male valve chamber.

20. A shutoff valve coupling as recited in claim 19 wherein said male shutoff valve further comprises a plunger slidably mounted in said chamber, said plunger slidable between an open position and a closed position, wherein said plunger has a frustum stage tapered toward said front opening, said frustum stage slidably positionable in said interior chamber when said plunger is in said closed position, means for biasing said frustum stage toward said sealing shoulder, thereby sliding said plunger into said closed position, and means for sealing said fluid passageway between said frustum stage and said sealing shoulder when said plunger is in said closed position, thereby occluding said fluid passageway, and further wherein said male plunger engages said female plunger when said male and female shutoff valves are in said open position.

* * * * *